US009581627B2

(12) United States Patent
Malone et al.

(10) Patent No.: US 9,581,627 B2
(45) Date of Patent: Feb. 28, 2017

(54) METHOD AND SYSTEM FOR TOMOGRAPHIC IMAGING

(71) Applicant: General Electric Company Global Research, Schenectady, NY (US)

(72) Inventors: Emma Rosa Malone, London (GB); David Simon Holder, London (GB); Simon Robert Arridge, London (GB); Gustavo Sato dos Santos, London (GB)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 237 days.

(21) Appl. No.: 13/897,129

(22) Filed: May 17, 2013

(65) Prior Publication Data
US 2013/0307566 A1 Nov. 21, 2013

Related U.S. Application Data

(60) Provisional application No. 61/649,471, filed on May 21, 2012.

(51) Int. Cl.
*G01R 27/28* (2006.01)
*G01R 27/08* (2006.01)
(Continued)

(52) U.S. Cl.
CPC ........... *G01R 27/02* (2013.01); *A61B 5/0536* (2013.01); *A61B 5/7235* (2013.01); *G01R 27/08* (2013.01);
(Continued)

(58) Field of Classification Search
CPC ........ G01R 27/02; G01R 27/26; G01R 27/08; A61B 5/0536; A61B 5/7235; G01N 27/025; G01N 17/00
(Continued)

(56) References Cited

U.S. PATENT DOCUMENTS 6,725,087 B1 * 4/2004 Rubinsky ............... G06Q 50/24
128/920
8,063,336 B2 * 11/2011 Gefter et al. ............ 219/121.52
(Continued)

FOREIGN PATENT DOCUMENTS

CN 101444422 A 6/2009
CN 201341881 Y 11/2009
(Continued)

OTHER PUBLICATIONS

Boverman et al., "Robust Linearized Image Reconstruction for Multifrequency EIT of the Breast", IEEE Transactions on Medical Imaging, IEEE Service Center, Piscataway, NJ, US, vol. 27, No. 10, Oct. 1, 2008, pp. 1439-1448.*
(Continued)

*Primary Examiner* — Son Le
*Assistant Examiner* — Raul Rios Russo
(74) *Attorney, Agent, or Firm* — Fletcher Yoder, P.C.

(57) ABSTRACT

Approaches are disclosed for electrical impedance tomography which apply a current to a region at two or more frequencies and acquire voltage measurements at each frequency to generate a set of multi-frequency voltage measurements. One or more images of the region are generated, using spectral constraints, based on the multi-frequency data.

21 Claims, 2 Drawing Sheets

(51) Int. Cl.
G01R 27/02 (2006.01)
G01R 27/26 (2006.01)
A61B 5/00 (2006.01)
A61B 5/053 (2006.01)
G01N 17/00 (2006.01)
G01N 27/02 (2006.01)

(52) U.S. Cl.
CPC ............ *G01R 27/26* (2013.01); *G01N 17/00* (2013.01); *G01N 27/025* (2013.01)

(58) Field of Classification Search
USPC .......... 324/76.11–76.83, 459–470, 600, 649, 324/71.1, 713–718
See application file for complete search history.

(56) References Cited

U.S. PATENT DOCUMENTS

| | | | | |
|---|---|---|---|---|
| 2004/0236253 | A1* | 11/2004 | Vortman | A61N 7/02 601/2 |
| 2005/0065901 | A1* | 3/2005 | Diong | 706/25 |
| 2006/0235286 | A1* | 10/2006 | Stone | A61B 5/02007 600/381 |
| 2008/0154136 | A1* | 6/2008 | Webler | A61B 8/0833 600/463 |
| 2009/0036794 | A1* | 2/2009 | Stubhaug | A61B 5/053 600/547 |
| 2009/0234244 | A1 | 9/2009 | Tanaka | |
| 2010/0198101 | A1* | 8/2010 | Song | A61B 5/0536 600/547 |
| 2010/0241034 | A1* | 9/2010 | Little | A61N 7/02 601/2 |
| 2010/0268109 | A1 | 10/2010 | Wang | |
| 2010/0292603 | A1* | 11/2010 | Shiffman et al. | 600/547 |
| 2011/0125203 | A1* | 5/2011 | Simon | A61N 1/40 607/2 |
| 2012/0059445 | A1* | 3/2012 | Stevenson | A61N 1/05 607/116 |
| 2013/0096395 | A1* | 4/2013 | Katra | A61B 5/0537 600/301 |
| 2013/0307566 | A1 | 11/2013 | Malone et al. | |
| 2014/0031713 | A1* | 1/2014 | Gaw | A61B 5/0537 600/547 |
| 2015/0038872 | A1 | 2/2015 | Halter | |
| 2015/0157240 | A1 | 6/2015 | Shoudy et al. | |

FOREIGN PATENT DOCUMENTS

| | | |
|---|---|---|
| CN | 102008303 A | 4/2011 |
| EP | 1915089 B1 | 4/2013 |
| WO | 2010052503 A1 | 5/2010 |

OTHER PUBLICATIONS

Brandstatter et al., "Direct estimation of Cole parameters in multifrequency EIT using a regularized Gauss-Newton method", Physiological Measurement, Institute of Physical Publishing, Bristol, GB, vol. 24, No. 2, Apr. 30, 2003, pp. 437-448.*

Romsauerova et al., "Multi-frequency electrical impedance tomography (EIT) of the adult human head: initial findings in brain tumours, arteriovenous malformations and chronic stroke, development of an analysis method and calibration", Physiological Measurement, Institute of Physical Publishing, Bristol, GB, vol. 27, No. 5, Apr. 20, 2006, p. S147-S161.*

Goharian, Mehran, et al.; "A Novel Approach for EIT Regularization via Spatial and Spectral Principal Component Analysis"; Physiological Measurement, vol. 28, Issue 9, Aug. 21, 2007; pp. 1001-1016.

Chatziioannidis, I, et al.; "Electrical Impedance Tomography: A new Study Method for Neonatal Respiratory Distress Syndrome?", Hippokratia, vol. 15, Issue 3, Jul.-Sep. 2011; pp. 211-215.

Malone, Emma, et al.; "Multifrequency Electrical Impedance Tomography Using Spectral Constraints"; IEEE Transactions on Medical Imaging; vol. 33, Issue 2, Feb. 2014; pp. 341-345.

Malone, Emma, et al.; "Stroke Type Differentiation Using Spectrally Constrained Multifrequency EIT: Evaluation of Feasibility in a Realistic Head model", Physiological Measurement, vol. 35, May 20, 2014; p. 1051-1066.

Fitzgerald et al., "Extraction of Electrical Characteristics from Pixels of Multifrequency EIT Images", Physiological Measurement, Institute of Physics Publishing, Bristol, GB, vol. No. 18, Issue No. 2, pp. 107-118, May 1, 1997.

PCT Search Report and Written Opinion issued in connection with corresponding Application No. PCT/US2013/041965 on Aug. 28, 2013.

Unofficial English translation of Chinese Office Action issued in connection with corresponding CN Application No. 201380026590.9 on Nov. 27, 2015.

* cited by examiner

METHOD AND SYSTEM FOR TOMOGRAPHIC IMAGING

CROSS-REFERENCE TO RELATED APPLICATIONS

This application is a non-provisional filing of U.S. Provisional Patent Application No. 61/649,471, entitled "METHOD OF IMAGING", filed May 21, 2012, which is herein incorporated by reference in its entirety for all purposes.

BACKGROUND

The subject matter disclosed herein relates generally to imaging, such as voltage or current injected electrical impedance tomography and/or magnetic induction tomography.

Electrical impedance tomography (EIT) is a medical imaging technique used to non-invasively probe the internal properties of an object or subject, such as the electrical properties of materials or internal structures within the object or subject. For example, in EIT systems, an estimate of the distribution of electrical conductivities of probed internal structures is made and utilized to reconstruct the conductivity and/or permittivity of the materials within the probed area or volume. In certain implementations, electrodes are used to apply an alternating current (or a voltage in other implementations) to the surface of the skin and the resulting potential is measured. Measurements are made from different points on the skin and an image of impedance within the body is created using image reconstruction techniques. Thus, electrical impedance tomography provides imaging information regarding the internal electrical properties inside a body based on voltage measurements made at the surface of the body.

Electrical impedance tomography is a non-invasive technique for imaging physiological and pathological body functions. The benefits of EIT applications in medicine lie in the possibility of obtaining high temporal resolution, and in the portability and limited cost of the scanner. The main limitation is the low spatial resolution, which is due to the reconstruction problem being generally ill-posed. The underlying principle is to exploit the electrical properties of biological tissues to extract information about the anatomy and physiology of organs. The physical parameter of interest in EIT is the complex impedance or real conductivity that, in the case of biological tissue, are frequency dependent. A small amount of current (or a voltage) is injected into the body and voltage measurements are acquired using peripheral electrodes. A reconstruction algorithm is implemented to image the impedance distribution of the subject in two or three dimensions.

BRIEF DESCRIPTION

In one embodiment, a method is provided for imaging a subject. The method comprises applying a current or voltage to a region of tissue at two or more frequencies. Voltage measurements are acquired at each frequency to generate a set of multi-frequency voltage measurements. One or more images of the region of tissue are generated, using spectral constraints, based on the multi-frequency data.

In another embodiment, a monitoring and processing system for use in electrical impedance tomography is provided. The monitoring and processing system comprises a monitor configured to drive an array of electrodes or magnetic coils; a processor configured to receive and process signals from the array of electrodes or magnetic coils; and a memory configured to store one or more routines. The one or more routines, when executed by the processor, cause acts to be performed comprising: driving one or more of the electrodes or magnetic coils to apply a current or voltage at two or more frequencies; acquiring voltage measurements at each frequency via the array of electrodes or magnetic coils to generate a set of multi-frequency voltage measurements; and generating, using spectral constraints, one or more images based on the multi-frequency data.

In a further embodiment, one or more non-transitory computer-readable media encoding routines are provided. The routines, when executed, cause acts to be performed comprising: accessing a set of multi-frequency voltage measurements; and generating, using spectral constraints, one or more images based on the multi-frequency data.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As described in more detail below, provided herein are embodiments of electrical impedance tomography (EIT) and/or magnetic induction tomography (MIT) methods and systems for performing multi-frequency imaging using spectral constraints. In one embodiment, current or voltage is injected into or induced in the body in a wide range of frequencies, such as through a pair or multiple pairs of electrodes (in EIT) or using magnetic coils (in MIT). Voltage measurements are acquired for each frequency on some or all of the remaining boundary electrodes or via the magnetic coils. In one implementation, boundary voltage data is employed to directly reconstruct the distribution of each tissue, rather than the difference in conductivity between each pair of frequencies. Given that the reconstructed parameter is frequency independent, this approach allows for the simultaneous use of multi-frequency data, thus imposing more constraints for the reconstruction problem. Furthermore this approach allows for use of frequency difference data in non-linear reconstruction algorithms.

Figure 1:
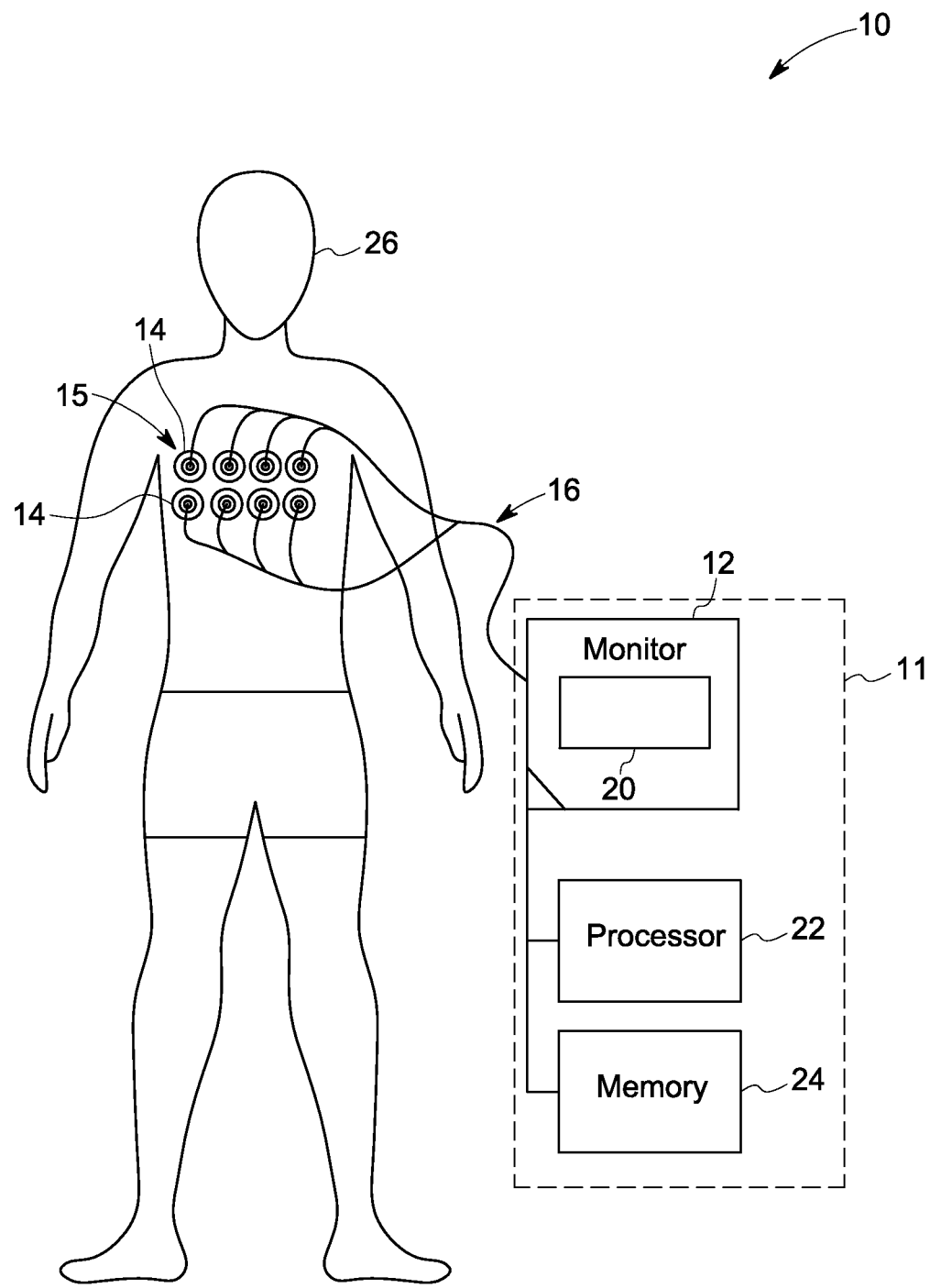
FIG. 1 is a schematic illustrating an embodiment of an electrical impedance spectroscopy or tomography system, in accordance with aspects of the present disclosure.

With the foregoing discussion in mind, an example of an EIT system 10 is illustrated in FIG. 1. For example, the EIT system 10 may be configured to estimate the electrical properties (e.g., conductivity and/or permittivity) inside a body or object using measurements obtained on the surface of the body or object (i.e., non-invasively). Depending on the system, tomographic representations spatially depicting the electrical properties (or values derived from such electrical properties) within the body may be generated and/or displayed.

In the depicted example, the system 10 includes a monitoring and processing system 11 including a monitor 12, a display 20, a processor 22, and a memory 24, as well as an array of sensors (i.e., electrodes 14) and communication cables 16. In the illustrated embodiment, the electrodes 14 are provided as an array on a surface 15 of a chest of a subject 26 above an interrogation region of the subject 26 (i.e., the subject's anatomy below the outer surface of the chest). However, it should be noted that in other embodiments, the electrodes 14 may be positioned on or about any desired portion of the subject's anatomy, such as but not limited to the chest, an arm, a leg, and so forth, or on any desired portion of another object or subject proximate to a desired interrogation region. By way of further example, in other embodiments the electrodes 14 may be positioned on the surface of the subject or object, near the surface of the subject or object, or penetrating the surface of the subject or object, depending on implementation-specific considerations. Accordingly, it should be noted that the electrodes 14 may take on a variety of different forms, such as surface-contacting electrodes, stand-off electrodes, capacitively coupled electrodes, conducting coils, antennas, and so forth. Additionally, the electrodes may be arranged in any desired spatial distribution, such as linear arrays, rectangular arrays, etc.

Further, different quantities (e.g., 8, 16, 32, and so forth) and arrangements (e.g., adhesive individual electrodes, electrodes provided on a pad, etc.) of electrodes 14 may be provided in different embodiments. In certain embodiments, coupling between the subject 26 and the electrodes 14 may be achieved by an adhesive portion (e.g., a tacky base layer) of the electrodes 14 or a component to which the electrodes 14 are attached. For example, in some embodiments, the electrodes 14 may be provided attached to or otherwise integrated with a compliant pad or substrate that may be positioned or placed on the subject 26.

During operation, the electrodes 14 communicate with the monitor 12, which may include one or more driving and/or controlling circuits for controlling operation of the electrodes 14, such as to generate electrical signals at each electrode. In one such embodiment, each electrode 14 is independently addressable by the drive or control circuitry. The drive and/or control functionality may be provided as one or more application specific integrated circuits (ASICs) within the monitor 12 or may be implemented using one or more general or special-purpose processors 22 used to execute code or routines for performing such control functionality.

In addition, one or more of the processors 22 may provide data processing functionality with respect to the signals read out using the electrodes 14. For example, a processor 22 may execute one or more stored processor-executable routines that may process signals derived from the measured electrical signals to generate numeric values or tomographic representations for review by a user, as discussed herein. Further, the routines executed by the processor 22 and/or the data processed by the processor 22 may be stored on a storage component (i.e., memory 22 or other suitable optical, magnetic, or solid-state storage structures in communication with the processor 22). Suitable storage structures include, but are not limited to, one or more memory chips, magnetic or solid state drives, optical disks, and so forth, suitable for short or long-term storage. The storage component may be local or remote from the processor 22 and/or system 10. For example, the storage component may be a memory 24 or storage device located on a computer network that is in communication with the processing component 22. In the present context, the storage component may also store programs and routines executed by the processing component 22, including routines for implementing the presently disclosed approaches.

While the foregoing generally describes aspects of an EIT imaging system with which the present techniques may be employed, as noted above, the present approaches may also be suitable for use in a magnetic induction tomography (MIT) system. In such an MIT system, magnetic coils, as opposed to electrodes 14, may be employed to inject or induce a current or voltage in the tissue of interest and to sense the measured parameters. For the purpose of the present disclosure, however, other components or aspects of a suitable MIT system may correspond to those of the generalized EIT system discussed above.

With the foregoing in mind, the following provides a brief introduction to EIT and MIT imaging principles. With respect to the mathematical foundation, the mathematical dependence of the conductivity distribution a of an object from the potential distribution u is described by Laplace's generalized equation:

$$\nabla(\sigma \nabla u) = 0 \qquad (1)$$

Reconstructing an image of the conductivity involves solving the forward and the inverse problems. In this context, the forward problem consists of determining the potential from knowledge of the conductivity distribution and the Neumann boundary conditions. The forward model $F:S_p \rightarrow S_d$ reveals how object parameters relate to acquired measurements. The objective of the inverse problem is to estimate the internal conductivity distribution of an object from the Neumann-to-Dirichlet map. An EIT image can be obtained via least-square minimization of a regularized objective functional $\phi(\sigma):R^n \rightarrow R$:

$$\sigma = \operatorname*{argmin}_{\sigma} \left\{ \frac{\|\xi(F(\sigma) - V)\|^2 + \tau \Psi(\sigma, \eta)}{\varphi(\sigma)} \right\} \qquad (2)$$

where $F(\sigma)$ is the forward model, $\xi \in R^{M \times M}$ is a weighting diagonal matrix of the residual $r(\sigma) = F(\sigma) - V$ and $\Psi(\sigma, \eta):R^K \rightarrow R$ is the regularization prior.

A simple approximation of the forward problem is obtained by truncating the Taylor series at the first derivative and considering:

$$F(\sigma) \approx F(\sigma_0) + J(\sigma - \sigma_0) \qquad (3)$$

where $\sigma_0$ is a fixed baseline. The difference in boundary voltages $\Delta V$ with respect to the baseline expressed in terms of the conductivity change $\Delta \sigma = \sigma - \sigma_0$ is:

$$\Delta V = F(\sigma) - F(\sigma_0) = J \Delta \sigma.$$

Therefore a variation in conductivity $\Delta \sigma$ with respect to a baseline can be reconstructed from knowledge of $\Delta V$ and the sensitivity matrix. Boundary measurements are acquired for $\sigma$ and $\sigma_0$ and subtracted to obtain the data $\Delta V$ while $J$ is computed in $\sigma_0$. The linear approximation may be employed to produce images of small, localized conductivity changes across time or frequency. However errors may be introduced in the case of large or widespread changes.

Non-linear approaches may be based on the iterative search for the global minimum of the objective functional. In such implementations, at each step the forward model is run and the hypothesis for $\sigma$ is updated. Methods may differ in the choice of regularization term and the criteria to select the minimization step and direction.

With respect to the various EIT imaging modalities, static imaging aims to reconstruct absolute conductivity values from a single data set. Absolute imaging has been attempted by various groups, however high sensitivity to uncertainty in the physical model and instrumentation errors have prevented the production of satisfactory images for use in a clinical or context. Instead, most EIT imaging is performed by referring measurements to a baseline and imaging conductivity changes, rather than absolute values. This produces contrast images, of which the absolute pixel values do not provide quantitative information. One advantage of difference imaging over absolute imaging is the suppression of geometric and instrumentation errors. However, a disadvantage is that a baseline must be identified.

Dynamic and multi-frequency EIT imaging are distinguished by the choice of baseline. In dynamic imaging, measurements are referred to a previous time point:

$$\Delta V_{TD} = V_t - V_{t_0} \quad (5)$$

Time-difference EIT allows for the imaging of impedance variations over time from small changes in the boundary voltages. In certain implementations of clinical imaging in biomedical studies, a time-difference method has been employed and an assumption of linearity made regarding changes in conductivity in the subject and the boundary voltage recording. Time-difference EIT imaging allows for monitoring of dynamic body functions such as lung ventilation or gastric emptying.

Multi-frequency EIT, or EIT-Spectroscopy (EITS), is based on the differences between the impedance spectra of tissues. Measurements are acquired simultaneously or in rapid sequence by varying the frequency of the injected current (or voltage) and are referred to a baseline frequency:

$$\Delta V_{FD} = V_\omega - V_{\omega_0}. \quad (6)$$

Frequency-difference EIT allows for the imaging of an event without information regarding the condition prior to the onset. This is useful in a medical context for producing diagnostic images of conditions such as acute stroke or breast cancer as patients are admitted into care after the onset of the pathology, and a baseline recording of the healthy tissue is not available.

Figure 2:
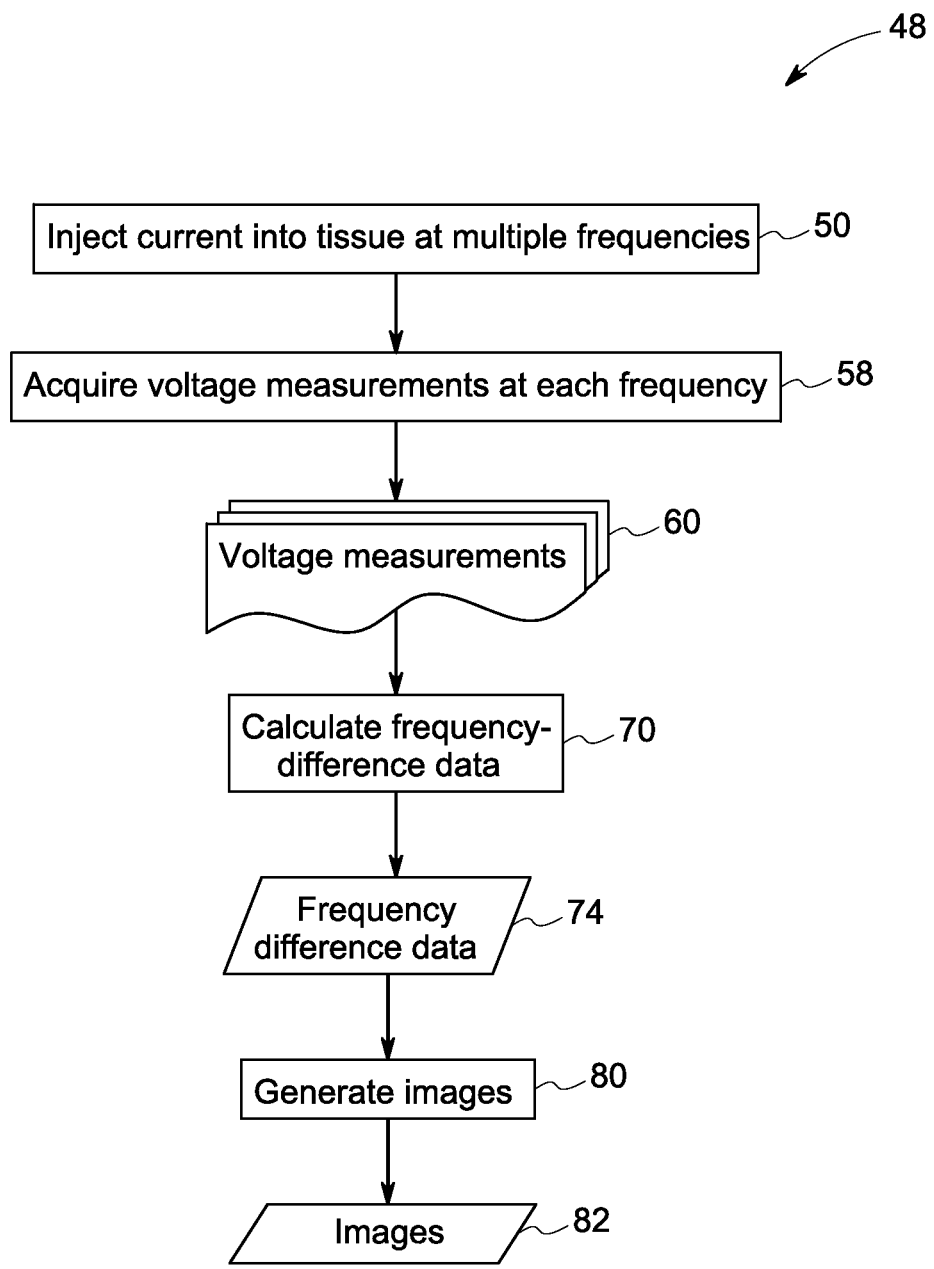
FIG. 2 depicts a flow chart of an embodiment of an algorithm for generating electrical impedance images, in accordance with aspects of the present disclosure.

With the foregoing discussion of EIT imaging and systems in mind, and turning to FIG. 2, the present approach is generally directed to performing multi-frequency EIT using spectral constraints. In one implementation, current or voltage is injected into the body through a pair or multiple pairs of electrodes in a range of frequencies. Voltage measurements are acquired for each frequency on some or all of the remaining boundary electrodes. Boundary voltage data is employed to directly reconstruct the distribution of each tissue, rather than the difference in conductivity between each pair of frequencies. Given that the reconstructed parameter is frequency independent, this approach allows for the simultaneous use of multi-frequency data, thus imposing more constraints for the reconstruction problem. Furthermore this approach allows for use of frequency difference data in non-linear reconstruction algorithms.

In this manner, an object may be imaged with frequency dependent conductivity distribution $\sigma(x, t, \omega)$, made-up of a limited number of tissues $\{t_1, \ldots, t_j, \ldots, t_T\}$ with distinct conductivity spectra. In one implementation, the object is modeled using a Finite Element Mesh with a mesh having E elements:

$$\sigma(x,t,\omega) = \{\sigma_1, \ldots, \sigma_n, \ldots, \sigma_E\}. \quad (7)$$

Boundary voltage measurements are acquired at multiple frequencies $\omega = \{\omega_1, \ldots, \omega_i, \ldots, \omega_F\}$.

In one embodiment, a priori knowledge of the conductivity spectra of tissues is employed to define the conductivity distribution in terms of the volume fraction value of tissues in the domain. If the conductivity values of each tissue is known exactly for each measurement frequency $\sigma(\omega_i, t_j) = \epsilon_{ij}$ then the conductivity of each element can be approximated by the linear combination of the conductivity of its component tissues:

$$\sigma(x, t, \omega_i) = \sum_{j=1}^{T} f_j(x, t) \epsilon_{ij} \quad (8)$$

where $0 < f_{nj} < 1$ and $\sum_{j=1}^{T} f_{nj} = 1$.

The relationship between conductivity and boundary voltages $V = \{V_1, \ldots, V_k, \ldots, V_D\}$ can be rewritten as:

$$V(\sigma, I) = V\left(\sum_{j=1}^{T} f_j(x,t)\epsilon_j(\omega), I\right) \quad (9)$$

therefore the chain rule yields, for $j=1, \ldots, T$:

$$\frac{\partial V(\omega)}{\partial f_j} = \frac{\partial V}{\partial \sigma}\frac{\partial \sigma}{\partial f_j} = \frac{\partial V}{\partial \sigma}\epsilon_j\bigg|_\omega \quad (10)$$

where $J(\sigma) = \{[J]_{kn} = \partial V_k / \partial \sigma_n\}$ is the Jacobian of the forward map.

The voltage measurements are acquired simultaneously or in rapid sequence, so that the distribution of each tissue is constant:

$$\sigma(x, \omega_i) = \sum_{j=1}^{T} f_j(x)\epsilon_{ij} \quad (11)$$

In certain embodiments, fraction images are reconstructed using a linear method if the relationship between the difference boundary voltages and change in conductivity across frequencies is approximately linear. Otherwise a non-linear method is implemented.

With respect to the linear implementation, such an implementation is suitable for treating problems for which the assumption of linearity between changes in conductivity in the subject and the boundary voltage recording is valid and the conductivity spectral of the component tissues are known. The linear approximation of the forward map is obtained by truncating the Taylor series at the first derivative and considering:

$$F(\sigma) \approx F(\sigma_0) + J(\sigma - \sigma_0) \quad (12)$$

where $\sigma_0$ is a fixed baseline. The difference in boundary voltages with respect to a baseline $\Delta V$ is expressed in terms of the conductivity change $\Delta \sigma = \sigma - \sigma_0$ as:

$$\Delta V(t,\omega) = F(\sigma(x,t,\omega)) - F(\sigma_0) = J(\sigma_0)\Delta\sigma(x,t,\omega). \quad (13)$$

Therefore, based on the fraction model:

$$\Delta V(t, \omega) = J(t_0, \omega_0) \cdot \Delta\left(\sum_{j=1}^{T} f_j(x, t)\epsilon_j(\omega)\right) \quad (14)$$

where $\Delta$ indicates a change over time or frequency. Measurements are repeated for several frequencies $\omega_1, \ldots, \omega_i, \ldots, \omega_F$ to obtain a matrix:

$$\begin{pmatrix} V(\omega_1) \\ \vdots \\ V(\omega_i) \\ \vdots \\ V(\omega_F) \end{pmatrix} = \qquad (15)$$

$$\begin{pmatrix} J(\omega_1)\epsilon_1(\omega_1) & \ldots & J(\omega_1)\epsilon_j(\omega_1) & \ldots & J(\omega_1)\epsilon_T(\omega_1) \\ \vdots & \ddots & \vdots & \ddots & \vdots \\ J(\omega_i)\epsilon_1(\omega_i) & \ldots & J(\omega_i)\epsilon_j(\omega_i) & \ldots & J(\omega_i)\epsilon_T(\omega_1) \\ \vdots & \ddots & \vdots & \ddots & \vdots \\ J(\omega_F)\epsilon_1(\omega_F) & \ldots & J(\omega_F)\epsilon_j(\omega_i) & \ldots & J(\omega_F)\epsilon_T(\omega_F) \end{pmatrix} \begin{pmatrix} f_1 \\ \vdots \\ f_j \\ \vdots \\ f_T \end{pmatrix}$$

A reference frequency $\omega_0$ is defined and the conductivity change over frequency is imaged. Assuming that $$\frac{\partial f_j}{\partial t} = 0$$

for $j=1, \ldots, T$ then:

$$\Delta_\omega \sigma = \sigma(\omega) - \sigma(\omega_0) = \qquad (16)$$

$$= \sum_{j=1}^{T} f_j(x,t)\epsilon_j(\omega) - \sum_{j=1}^{T} f_j(x,t)\epsilon_j(\omega_0) =$$

$$= \sum_{j=1}^{T} f_j(x,t)(\epsilon_j(\omega) - \epsilon_j(\epsilon_0)) \approx$$

$$\approx \sum_{j=1}^{T} f_j(x,t)\Delta_\omega \epsilon_j.$$

Therefore:

$$\begin{pmatrix} f_1 \\ \vdots \\ f_j \\ \vdots \\ f_T \end{pmatrix} = \qquad (17)$$

$$\begin{pmatrix} J(\omega_{0_1})\Delta_\omega \epsilon_1(\omega_1) & \ldots & J(\omega_{0_1})\Delta_\omega \epsilon_j(\omega_1) & \ldots & J(\omega_{0_1})\Delta_\omega \epsilon_T(\omega_2) \\ \vdots & \ddots & \vdots & \ddots & \vdots \\ J(\omega_{0_i})\Delta_\omega \epsilon_1(\omega_i) & \ldots & J(\omega_{0_i})\Delta_\omega \epsilon_j(\omega_i) & \ldots & J(\omega_{0_i})\Delta_\omega \epsilon_T(\omega_1) \\ \vdots & \ddots & \vdots & \ddots & \vdots \\ J(\omega_{0_F})\Delta_\omega \epsilon_1(\omega_F) & \ldots & J(\omega_{0_F})\Delta_\omega \epsilon_j(\omega_i) & \ldots & J(\omega_{0_F})\Delta_\omega \epsilon_T(\omega_F) \end{pmatrix}^{-1}$$

$$\begin{pmatrix} \Delta_\omega V(\omega_1) \\ \vdots \\ \Delta_\omega V(\omega_i) \\ \vdots \\ \Delta_\omega V(\omega_F) \end{pmatrix}$$

If the same reference conductivity $\sigma(\omega_0)$ is used for each frequency we have that $J = J(\omega_{0_1}) = \ldots = J(\omega_{0_F})$ and equation (17) can be rewritten using the Kronecker multiplication. If the matrix $\Delta\epsilon$ is defined as:

$$\Delta\epsilon = \begin{pmatrix} \Delta_\omega \epsilon_1(\omega_1) & \ldots & \Delta_\omega \epsilon_j(\omega_1) & \ldots & \Delta_\omega \epsilon_T(\omega_1) \\ \vdots & \ddots & \vdots & \ddots & \vdots \\ \Delta_\omega \epsilon_1(\omega_i) & \ldots & \Delta_\omega \epsilon_j(\omega_i) & \ldots & \Delta_\omega \epsilon_T(\omega_i) \\ \vdots & \ddots & \vdots & \ddots & \vdots \\ \Delta_\omega \epsilon_1(\omega_F) & \ldots & \Delta_\omega \epsilon_j(\omega_F) & \ldots & \Delta_\omega \epsilon_T(\omega_F) \end{pmatrix} \qquad (18)$$

then:

$$\Delta\epsilon \otimes J = \begin{pmatrix} J\Delta_\omega \epsilon_1(\omega_1) & \ldots & J\Delta_\omega \epsilon_j(\omega_1) & \ldots & J\Delta_\omega \epsilon_T(\omega_1) \\ \vdots & \ddots & \vdots & \ddots & \vdots \\ J\Delta_\omega \epsilon_1(\omega_i) & \ldots & J\Delta_\omega \epsilon_j(\omega_i) & \ldots & J\Delta_\omega \epsilon_T(\omega_i) \\ \vdots & \ddots & \vdots & \ddots & \vdots \\ J\Delta_\omega \epsilon_1(\omega_F) & \ldots & J\Delta_\omega \epsilon_j(\omega_F) & \ldots & J\Delta_\omega \epsilon_T(\omega_F) \end{pmatrix} \qquad (19)$$

where $\otimes$ is the external or Kronecker multiplication. Therefore, the fraction images $f_j \forall j=1, \ldots, T$ are recovered using the equation:

$$\begin{pmatrix} f_1 \\ \vdots \\ f_j \\ \vdots \\ f_T \end{pmatrix} = (\Delta\epsilon \otimes J)^{-1} \begin{pmatrix} \Delta_\omega V(\omega_1) \\ \vdots \\ \Delta_\omega V(\omega_i) \\ \vdots \\ \Delta_\omega V(\omega_F) \end{pmatrix} \qquad (20)$$

where $$(\Delta\epsilon \otimes J)^{-1} = \Delta\epsilon^{-1} \otimes J^{-1} \qquad (21)$$

is the inverse of the Kronecker product.

With respect to the non-linear implementation, the non-linear implementation is suitable for situations where the relationship between changes in conductivity in the subject and the boundary voltage recording is non-linear and the conductivity spectral of the component tissues are approximately known.

Fractions may be reconstructed by iteratively minimizing a regularized objective function using a non-linear method:

$$f = \underset{f}{\operatorname{argmin}}(\varphi(f)) \qquad (22)$$

where f is the vector of fraction values $f_{n_j}$, where n runs over the elements in the mesh, and j over the tissues. The fraction model allows for the use of frequency-difference data in the objective function:

$$\phi(f) = \Sigma_i \tfrac{1}{2}(\|F(\sigma_i) - F(\sigma_0) - (V_i - V_0)\|^2 + \alpha \Psi(f)) \qquad (23)$$

where the data can be normalized to a certain frequency. Absolute or time-difference data can also be used.

For example using Tikhonov regularization, the objective function for fraction reconstruction becomes:

$$\varphi(f) = \frac{1}{2}\sum_i \left\| \left(F\left(\sum_j f_j \epsilon_{ij}\right) - F\left(\sum_j f_j \epsilon_{0j}\right)\right) - \Delta V_i \right\|^2 + \qquad (24)$$

-continued $$\alpha \sum_i \left\| \sum_j (f_j \Delta \epsilon_{ij}) \right\|^2 =$$

$$= \frac{1}{2} \sum_{ik} \left[ \left( F_k \left( \sum_j f_j \epsilon_{ij} \right) - F_k \left( \sum_j f_j \epsilon_{0j} \right) \right) - \Delta V_{ik} \right]^2 +$$

$$\alpha \sum_{in} \left[ \sum_j (f_{jn} \Delta \epsilon_{ij}) \right]^2$$

where i runs over frequencies and k over measurements. Other regularization methods, such as Total Variation or Markov Random Field, can be used.

In this case, the objective function is differentiable, and the gradient is:

$$[\nabla f(f)]_{jn} = \Sigma_{ik}[(J_{kn}(\Sigma_r f_r \epsilon_{it})\epsilon_{ij} - J_{kn}(\Sigma_r f_r \epsilon_{0j})\epsilon_{0j})*(F_k(\Sigma_r f_r \epsilon_{ij}) - F_k(\Sigma_r f_r \epsilon_{0j}) - \Delta V_{ik})] + \alpha \Sigma_i [\Delta \epsilon_{ij} * \Sigma_r (f_m \Delta \epsilon_{it})] \quad (25)$$

where J is the Jacobian of the forward map F(σ).

The Hessian is approximated by:

$$[H(f)]_{m_p n_l} = \Sigma_{ik}[(J_{m_j k}(\Sigma_r f_r \epsilon_{it})\epsilon_{ij} - J_{m_j k}(\Sigma_r f_r \epsilon_{0r})\epsilon_{0j})*(J_{kn_l}(\Sigma_r f_r \epsilon_{it})\epsilon_{il} - J_{kn_l}(\Sigma_r f_r \epsilon_{0l})\epsilon_{0l})] + \alpha \Sigma_i (\Delta \epsilon_{ij} * \Delta \epsilon_{il}) \quad (26)$$

where $m_j$ and $n_l$ run over all elements and tissues. Therefore the fraction images $f_j \forall j=1, \ldots, T$ may be reconstructed simultaneously by using a second order descent method, such as Damped Gauss-Newton or Non-linear Conjugate Gradients. or Gradient Projection. The reconstruction can be constrained so that $0 < f_{nj} < 1$ and $\Sigma_{j=1}^T f_{nj} = 1$.

With the foregoing in mind, and turning to FIG. 2, the present disclosure provides a method 48 of imaging a subject that suitable for use in electrical impedance tomography. In one implementation, the subject is modeled using a finite element approach. In certain embodiments, the region of the subject (e.g., patient) being imaged consists of a plurality of tissue types (i.e., two or more types of tissue). In such embodiments, to the extent that predetermined tissue conductivity spectra are available and are used in the imaging operations associated with the method 48, such predetermined tissue conductivity spectra consist of known or predetermined spectral conductivity data for at least the tissue types expected to be present in the subject within the imaged region. In one implementation, current or voltage is injected (block 50) into the tissues of the subject, such as through a pair or multiple pairs of electrodes, in a range of frequencies.

Voltage measurements 60 are acquired (block 58) for each frequency on some or all of the remaining boundary electrodes. In one embodiment, the boundary voltage measurements 60 comprise a set of multi-frequency measurements. In certain implementations, the boundary voltage measurements 60 of the subject are obtained at a single measurement time rather than at two or more measurement times separated by some interval of time. Such an implementation may offer advantages since a single multi-frequency measurement of the subject can be used to construct an image, rather than taking two or more measurement separated in time.

Turning back to FIG. 2, a set of frequency-difference data 74 is calculated (block 70) from the set of multi-frequency measurements. In one implementation, the step of calculating (block 70) frequency-difference data includes identifying a baseline from the set of multi-frequency measurements and calculating the frequency-difference data with respect to the baseline.

The frequency-difference data 74 is used to generate (block 80) one or more images 82 of the subject. In one embodiment, the act of generating (block 80) the images 82 includes the step of forming an image 82 using a frequency independent approach that employees the frequency-difference data, as discussed herein. In addition, in certain implementations, the act of generating the images 82 may employ spectral constraints, as discussed herein. The act of generating images 82 may include the act of defining the conductivity distribution of the subject in terms of a volume fraction of tissues, as discussed above. Similarly, the act of generating images 82 may use the boundary voltage measurements 60 to reconstruct the volume fraction distribution of each tissue or tissue type within the region undergoing imaging, as discussed herein.

The disclosed method may be useful for generating diagnostic images of conditions such as acute stroke or breast cancer where prior images or data may be unavailable. That is, in general, this approach may be useful for patients that are admitted into care after the onset of a pathology, where a previous recording of healthy tissue is not available. As the present method uses frequency differences to construct an image rather than measurements taken at different times, imaging can be performed quickly and absolute conductivity values can be gained from a single data set. In certain implementations, the boundary voltage data may be used to directly reconstruct the volume fraction distribution of each component tissue, rather than the difference in conductivity between pairs of frequencies.

Technical effects of the invention include performing multi-frequency EIT using spectral constraints. Voltage measurements are acquired for a range of frequencies using electrodes disposed at various points on the patient. The boundary voltage data is used to directly reconstruct the distribution of each tissue, rather than the difference in conductivity between each pair of frequencies. This approach allows for the simultaneous use of multi-frequency data, thus imposing more constraints for the reconstruction problem.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for imaging a subject, comprising:
   applying a current or voltage to a region of tissue comprising multiple tissue types at two or more frequencies;
   acquiring voltage measurements at each frequency of a set of frequencies to generate a set of multi-frequency voltage measurements; and
   generating, using spectral constraints, one image of the region of tissue based on simultaneous use of the set of multi-frequency voltage measurements, wherein the spectral constraints are based on prior knowledge of the differences in the impedance of the tissue types of the region of tissue with respect to the differences in the frequencies of the set of frequencies.

2. The method of claim 1, comprising modeling the region of tissue using a finite element mesh and applying a volume fraction describing a distribution of the tissue types to each element of the finite element mesh to estimate a conductivity distribution.

3. The method of claim 1, wherein the current is applied to the region of tissue and the voltage measurements acquired via a pair or multiple pairs of electrodes.

4. The method of claim 1, wherein the voltage measurements at each frequency are acquired simultaneously.

5. The method of claim 1, wherein the voltage measurements at each frequency are acquired at two or more measurement times.

6. The method of claim 1, further comprising:
calculating frequency-difference data from the set of multi-frequency voltage measurements;
wherein generating the one image of the region of the tissue is based on the frequency difference data.

7. The method of claim 6, wherein calculating frequency difference data comprises identifying a baseline from the set of multi-frequency voltage measurements and calculating the frequency-difference data with respect to the baseline.

8. The method of claim 1, wherein generating the one image of the region of the tissue comprises defining a conductivity distribution of the region in terms of a volume fraction of the tissue types.

9. The method of claim 1, wherein generating the one image of the region of the tissue comprises using the multi-frequency voltage measurements to reconstruct a volume fraction distribution of each tissue type within the region of the tissue.

10. A monitoring and processing system for use in tomography, comprising:
a monitor configured to drive an array of electrodes or magnetic coils;
a processor configured to receive and process signals from the array of electrodes or magnetic coils; and
a memory configured to store one or more routines which, when executed by the processor, cause acts to be performed comprising:
driving one or more of the electrodes or magnetic coils to apply a current or voltage at two or more frequencies;
acquiring voltage measurements at each frequency via the array of electrodes or magnetic coils to generate a set of multi-frequency voltage measurements; and
generating, using spectral constraints, one image of a region of tissue based on simultaneous use of the multi-frequency voltage measurements, wherein the spectral constraints are based on prior knowledge of the differences in the impedance for of tissue types of the region of tissue with respect to differences between the two or more frequencies.

11. The monitoring and processing system of claim 10, wherein the one or more routines, when executed by the processor, cause further acts to be performed comprising displaying the one or more images on a display of the monitor.

12. The monitoring and processing system of claim 10, wherein the voltage measurements at each frequency are acquired simultaneously.

13. The monitoring and processing system of claim 10, wherein the one or more routines, when executed by the processor, cause further acts to be performed comprising:
calculating frequency-difference data from the set of multi-frequency voltage measurements;
wherein generating the image of a region of tissue is based on the frequency difference data.

14. The monitoring and processing system of claim 13, wherein calculating frequency difference data comprises identifying a baseline from the set of multi-frequency voltage measurements and calculating the frequency-difference data with respect to the baseline.

15. The monitoring and processing system of claim 10, wherein generating the one image comprises using the multi-frequency voltage measurements to reconstruct a volume fraction distribution of each tissue type within the region.

16. The monitoring and processing system of claim 10, wherein generating the one image comprises defining a conductivity distribution of the region in terms of a volume fraction of tissue types.

17. One or more non-transitory computer-readable media encoding routines which, when executed, cause acts to be performed comprising:
accessing a set of multi-frequency voltage measurements obtained at multiple frequencies of a set of frequencies; and
generating, using spectral constraints, one image based on simultaneous use of the multi-frequency data, wherein the spectral constraints are based on prior knowledge of the differences in impedance of the tissue types of the region of tissue with respect to the differences between the frequencies of the set of frequencies.

18. The one or more non-transitory computer-readable media of claim 17, wherein the routines, when executed, cause further acts to be performed comprising:
driving one or more of the electrodes to apply a current at two or more frequencies of the set of frequencies; and
acquiring voltage measurements at each frequency via the array of electrodes to generate the set of multi-frequency voltage measurements.

19. The one or more non-transitory computer-readable media of claim 17, wherein the set of multi-frequency voltage measurements are acquired simultaneously.

20. The one or more non-transitory computer-readable media of claim 17, wherein the routines, when executed, cause further acts to be performed comprising:
calculating frequency-difference data from the set of multi-frequency voltage measurements;
wherein generating the one image is based on the frequency difference data.

21. The one or more non-transitory computer-readable media of claim 20, wherein calculating frequency difference data comprises identifying a baseline from the set of multi-frequency voltage measurements and calculating the frequency-difference data with respect to the baseline.

* * * * *